United States Patent
Aoki et al.

(10) Patent No.: US 12,297,419 B2
(45) Date of Patent: May 13, 2025

(54) CULTURE DEVICE

(71) Applicant: PHC Corporation, Ehime (JP)

(72) Inventors: Hikaru Aoki, Gunma (JP); Kousuke Honda, Ehime (JP); Hiroki Hirai, Kagawa (JP); Akito Sawai, Mie (JP); Manami Baba, Gunma (JP)

(73) Assignee: PHC CORPORATION, Ehime (JP)

( * ) Notice: Subject to any disclaimer, the term of this patent is extended or adjusted under 35 U.S.C. 154(b) by 846 days.

(21) Appl. No.: 17/193,534

(22) Filed: Mar. 5, 2021

(65) Prior Publication Data
US 2021/0189318 A1    Jun. 24, 2021

Related U.S. Application Data

(63) Continuation of application No. PCT/JP2019/031917, filed on Aug. 14, 2019.

(30) Foreign Application Priority Data

Sep. 6, 2018   (JP) .................................. 2018-166645

(51) Int. Cl.
*C12M 1/34*      (2006.01)
*C12M 1/12*      (2006.01)

(52) U.S. Cl.
CPC ............ *C12M 41/00* (2013.01); *C12M 37/04* (2013.01); *C12M 41/12* (2013.01)

(58) Field of Classification Search
CPC ...... C12M 41/00; C12M 37/04; C12M 41/12; C12M 41/34; C12M 41/14
See application file for complete search history.

(56) References Cited

U.S. PATENT DOCUMENTS

| | | | |
|---|---|---|---|
| 5,090,617 A * | 2/1992 | Swan ..................... | A01K 41/00 236/3 |
| 5,418,131 A | 5/1995 | Butts | |
| 5,773,287 A * | 6/1998 | Binder .................. | C12M 41/14 219/385 |
| 6,297,047 B1 * | 10/2001 | Butts ........................ | A61L 2/10 219/400 |
| 10,918,755 B2 * | 2/2021 | Hitomi ................... | C12M 41/14 |

(Continued)

FOREIGN PATENT DOCUMENTS

| DE | 69534425 T2 | 6/2006 |
|---|---|---|
| JP | H03-065176 A | 3/1991 |

(Continued)

OTHER PUBLICATIONS

Machine Translation of JP H0365176 from Espacenet, downloaded Dec. 2023 (Year: 2023).*

(Continued)

*Primary Examiner* — William H. Beisner
*Assistant Examiner* — Danielle B Henkel
(74) *Attorney, Agent, or Firm* — Rimon P.C.

(57) ABSTRACT

This culture device comprises: an inner box having a culture space formed on the inside thereof; an outer box which covers the outside of the inner box with a first space formed therebetween; a $CO_2$ sensor which is positioned in the first space and has a first end thereof exposed to the culture space; and a restricting member which restricts the flow of a fluid towards the $CO_2$ sensor within the first space.

10 Claims, 2 Drawing Sheets

(56) References Cited

U.S. PATENT DOCUMENTS

| | | | | |
|---|---|---|---|---|
| 2002/0047311 A1* | 4/2002 | Hugh | ............... | C12M 41/14 |
| | | | | 307/116 |
| 2005/0084956 A1* | 4/2005 | Tamaoki | ............... | C12M 41/14 |
| | | | | 435/303.1 |
| 2006/0148094 A1* | 7/2006 | Reinhardt | ............ | C12M 41/14 |
| | | | | 436/43 |
| 2010/0173401 A1* | 7/2010 | Kobayashi | ............ | C12M 41/12 |
| | | | | 435/303.1 |
| 2016/0010048 A1* | 1/2016 | Tokumaru | ............ | C12M 41/14 |
| | | | | 435/303.1 |

FOREIGN PATENT DOCUMENTS

| | | |
|---|---|---|
| JP | 2010-154793 A | 7/2010 |
| JP | 2017-035013 A | 2/2017 |

OTHER PUBLICATIONS

International Search Report issued in corresponding International Patent Application No. PCT/JP2019/031917, dated Nov. 12, 2019, with English translation.

Extended European Search Report dated Aug. 20, 2021 issued in the corresponding European Patent Application No. 19857394.1.

* cited by examiner

CULTURE DEVICE

CROSS-REFERENCE OF RELATED APPLICATIONS

This application is a Continuation of International Patent Application No. PCT/JP2019/031917, filed on Aug. 14, 2019, which in turn claims the benefit of Japanese Application No. 2018-166645, filed on Sep. 6, 2018, the entire disclosures of which Applications are incorporated by reference herein.

TECHNICAL FIELD

The present invention relates to a culture apparatus.

BACKGROUND ART

A culture apparatus is known, which includes a means for supplying a carbon dioxide ($CO_2$) gas to a culture space, and a $CO_2$ sensor for detecting $CO_2$ concentration in the culture space, and which controls a supply rate of $CO_2$ gas in accordance with a detection result of the $CO_2$ sensor (e.g., Patent Literature (hereinafter, referred to as "PTL") 1). With such a configuration, the $CO_2$ concentration in the air in the culture space is controlled to a concentration suitable for culture of cells, microorganisms, and the like.

In some type of such a culture apparatus, a $CO_2$ sensor (e.g., an IR sensor of an infrared light detection system) is disposed inside a sensor box disposed outside an inner box of the culture apparatus. Air in the culture apparatus is drawn into the sensor box through a pipe, and $CO_2$ concentration is detected by the $CO_2$ sensor. By heating the inside of the sensor box, the temperature of the sensor box is kept constant and dew condensation is prevented, and as a result, the $CO_2$ concentration can be accurately detected by the $CO_2$ sensor in the sensor box.

CITATION LIST

Patent Literature

PTL 1
Japanese Patent Application Laid-Open No. 2017-035013

SUMMARY OF INVENTION

Technical Problem

However, in such a configuration in which the air in the culture space is drawn into the sensor box and $CO_2$ concentration in the air is detected, the pipe for drawing the air into the sensor box is required. Accordingly, providing the pipe causes an increase in the cost and size of the culture apparatus.

The present invention has been devised to solve such a problem, and aims to reduce the cost and size of a culture apparatus.

Solution to Problem

In order to solve the above-mentioned conventional problem, the culture apparatus of the present invention is configured to include: an inner box having a culture space formed inside; an outer box covering an outside of the inner box with a first space therebetween; a $CO_2$ sensor disposed in the first space such that a first end of the $CO_2$ sensor is exposed to the culture space; and a regulation member that regulates a flow of a fluid toward the $CO_2$ sensor in the first space.

Advantageous Effects of Invention

According to the present invention, it is possible to reduce the cost and size of a culture apparatus.

DESCRIPTION OF EMBODIMENTS

Figure 1:
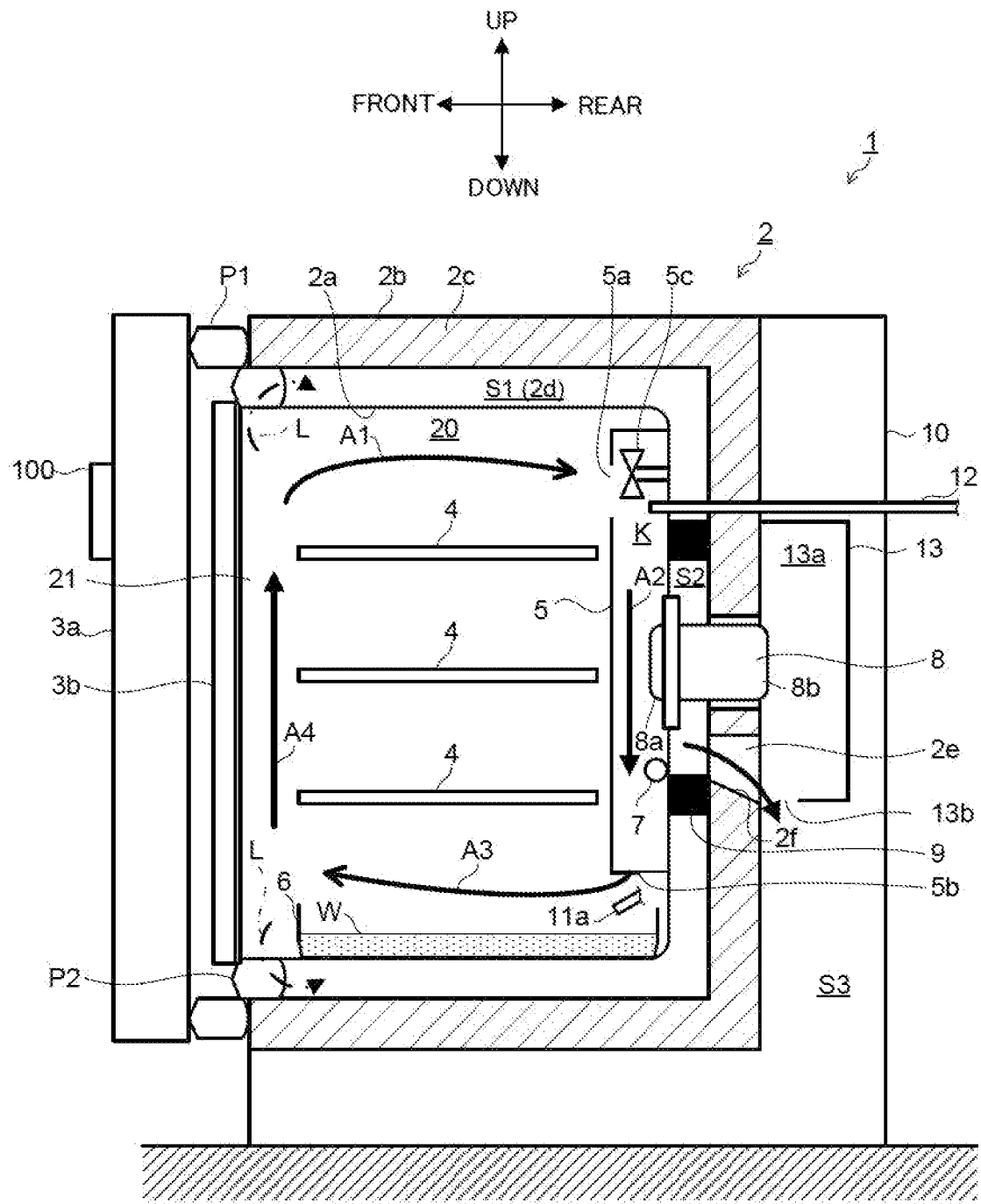
FIG. 1 illustrates a schematic longitudinal section of a culture apparatus of an embodiment of the present invention as seen from the right side.

Hereinafter, a culture apparatus according to an embodiment of the present invention will be described with reference to the accompanying drawings. The following embodiments are merely illustrative, and various modifications and/or applications of techniques which are not specified in the following embodiments are not excluded. In addition, the configurations of the embodiments can be variously modified and implemented without departing from the spirit thereof. Further, the configurations of the embodiments can be selected as necessary, or can be appropriately combined.

In the following description, the side of the culture apparatus which the user faces during usage of the culture apparatus (the side with below-described outer door 3a and inner door 3b) is referred to as "front" and the side opposite to the front is referred to as "rear." In addition, the left and right are defined with reference to the case of viewing from the front to the rear.

Note that, in all the figures for explaining the embodiments, the same elements are denoted by the same reference numerals in principle, and the description thereof may be omitted.

[1. Configuration]

Figure 2:
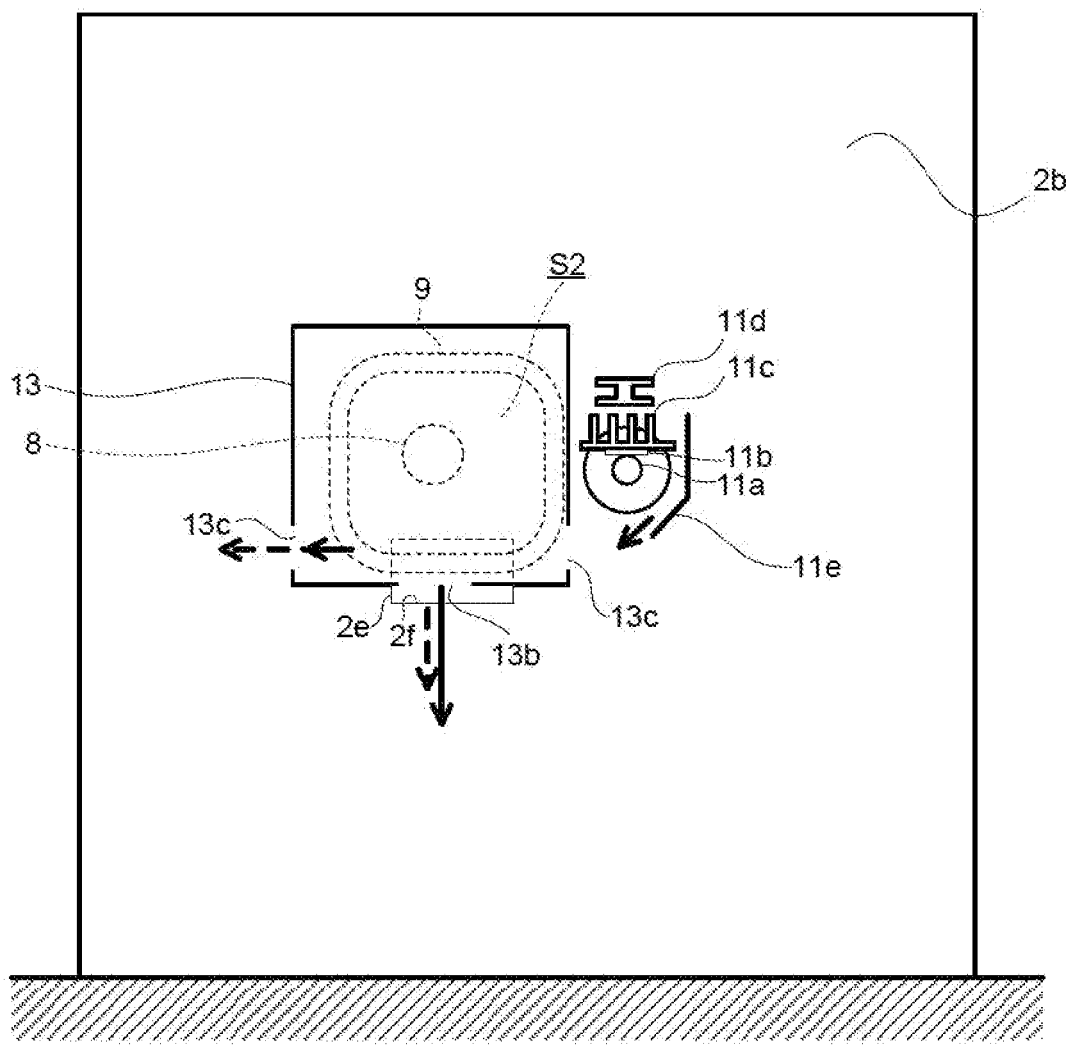
FIG. 2 schematically illustrates the back surface of the culture apparatus of an embodiment of the present invention, with a cover being removed.

Culture apparatus 1 in the present embodiment will be described with reference to FIGS. 1 and 2. FIG. 1 illustrates a schematic longitudinal section of the culture apparatus of the present embodiment as seen from the right side. FIG. 2 schematically illustrates the back surface of the culture apparatus of the present embodiment, with a cover being removed.

Culture apparatus 1 illustrated in FIGS. 1 and 2 is an apparatus for growing a culture such as a cell or a microorganism. Culture apparatus 1 is configured to include substantially box-shaped heat insulation box 2 having culture space 20 formed inside and opening 21 formed in the front surface, outer door 3a and inner door 3b for opening and closing opening 21. Culture space 20 is vertically compartmentalized by a plurality of (here, three) shelves 4. Packing P1 is disposed on the outer edge of outer door 3a.

As will be described later, in order to achieve an appropriate environment for culturing cells, microorganisms, and the like, culture space 20 is controlled such that the temperature, humidity, and $CO_2$ concentration are maintained within respective appropriate ranges.

Heat insulation box 2 includes substantially box-shaped inner box 2a having culture space 20 formed inside, and substantially box-shaped outer box 2b that covers the outside of inner box 2a.

Outer box 2b is provided, on its inner surface side, with heat insulation material 2c. Space S1 is formed between the inner surface of heat insulation material 2c of outer box 2b and the outer surface of inner box 2a in such a manner as to cover the upper, lower, left, right, and rear sides of inner box 2a. This space S1 is filled with air; the air layer (so-called air jacket) 2d is formed in space S1. Space S1 corresponds to the first space in the present invention. An opening is located in the front part of space S1, and this opening is sealed with packing P2. Inner door 3b and packing P2 ensure the hermeticity of culture space 20.

In culture space 20, vertically extending duct 5 is disposed on the back surface of inner box 2a. Gas passage K for the air containing $CO_2$ and the like is formed inside duct 5. Culture apparatus 1 sucks the air containing $CO_2$ and the like in culture space 20 through suction port 5a formed in an upper portion of duct 5, and blows out the air into culture space 20 through blow-out port 5b formed in a lower portion of duct 5. Thus, forced circulation of the air as indicated by arrows A1, A2, A3, and A4 takes place. Circulation blower 5c for causing such forced circulation is disposed in duct 5.

Humidification tray 6 for storing humidification water W is disposed between the lower portion of duct 5 and the bottom plate of inner box 2a. Humidification tray 6 is heated by a heater wire (not illustrated) disposed on the bottom plate of inner box 2a, so that water W evaporates.

Inner box 2a is provided with $CO_2$ sensor 8 for detecting $CO_2$ concentration in the air in culture space 20. The $CO_2$ sensor is an IR sensor of an infrared light detection system. In the IR sensor, a light-emitting element irradiates the air entering the inside of the sensor with infrared light, this infrared light is received by a light-receiving element, and $CO_2$ concentration in the air according to the transmittance of infrared light is detected.

Leading end 8a (one end) of this $CO_2$ sensor 8 is exposed to culture space 20, more specifically, to gas passage K in duct 5, and rear end 8b (second end) of this $CO_2$ sensor 8 is attached to heat insulation material 2c. An opening (not illustrated) for introducing the air between the light-emitting element and the light-receiving element is formed in leading end 8a of $CO_2$ sensor 8.

In space S1, that is, in air layer 2d, sealing material 9 is disposed around the $CO_2$ sensor. Sealing material 9 is a frame body whose upper side, right side, lower side, and left side are formed integrally. Sealing material 9 is disposed in close contact with the outer surface of inner box 2a and the inner surface of outer box 2b (specifically, the inner surface of heat insulation material 2c) such that $CO_2$ sensor 8 is positioned in the frame. That is, frame-shaped sealing material 9 is disposed to surround $CO_2$ sensor 8 from above, below, left, and right. Thus, sealed space S2 for providing a seal around $CO_2$ sensor 8 from above, below, left, and right is formed. Sealing material 9 corresponds to the regulation member in the present invention, and sealed space S2 corresponds to the second space in the present invention.

In addition, ultraviolet lamp 7 is disposed in duct 5 in order to sterilize the air flowing through duct 5 and thus culture space 20, and water W in humidification tray 6 below blow-out port 5b of duct 5.

Further, culture apparatus 1 receives, from operation device 100 disposed on outer door 3a, instruction inputs such as an instruction for starting and stopping culture apparatus 1, a target temperature (e.g., 37° C.), a target humidity (e.g., 93% RH), and/or a target concentration (e.g., 5%) of a $CO_2$ gas in culture space 20. A controller (not illustrated) controls the temperature, humidity, and $CO_2$ concentration in culture space 20 such that the temperature, humidity, and $CO_2$ concentration are at the above-mentioned target values.

The back and bottom surfaces of outer box 2b of heat insulation box 2 are covered with cover 10. The space between the back surface of outer box 2b and cover 10 forms mechanical room S3 for disposing various equipment therein. Gas supply device 12 for supplying a $CO_2$ gas to culture space 20, sensor box 13, a temperature sensor (not illustrated) for measuring the temperature in culture space 20, and an electrical box (not illustrated) for accommodating electrical components such as the control device are disposed in mechanical room S3.

Rear end 8b of $CO_2$ sensor 8 is exposed in mechanical room S3. Sensor box 13 is a box that opens forward, and covers rear end 8b of $CO_2$ sensor 8 from the rear in mechanical room S3. A temperature adjustment device is disposed in sensor box 13. By keeping the temperature of inner space 13a of sensor box 13 within a predetermined range by this temperature adjustment device, the sensitivity of the detection accuracy of $CO_2$ sensor 8 is kept constant.

In addition, opening 13b is formed in the bottom wall of sensor box 13 and opening 13c is formed in the lower portion of the right side wall and the lower portion of the left side wall of sensor box 13.

Passage 2e is formed in heat insulation material 2c below $CO_2$ sensor 8. This passage 2e communicates with sealed space S2 and mechanical room S3, and, in the present embodiment, also communicates with the inner space of sensor box 13. Bottom surface 2f of passage 2e is an inclined surface inclined downward from sealed space S2 toward mechanical room S3.

Further, as illustrated in FIG. 2, dew condensation member 11a is disposed on the back surface of heat insulation box 2. This dew condensation member 11a is inserted into culture space 20 from mechanical room S3. It is preferable that dew condensation member 11a have higher conductivity, and the dew condensation member is, for example, a round bar with a predetermined length that is made of aluminum, silver or the like. Peltier element 11b is disposed on an end of dew condensation member 11a within mechanical room S3 such that the heat-absorbing surface of the Peltier element 11b faces the end. The dew condensation member is cooled by the heat-absorbing surface. Accordingly, dew condensation water is generated on the surface of dew condensation member 11a in culture space 20, and consequently, the humidity in culture space 20 can be controlled within a predetermined range. Note that, the dew condensation water generated on the surface of dew condensation member 11a drips from dew condensation member 11a into humidification tray 6.

Further, comb-shaped heat sink 11c disposed on the heating surface of Peltier element 11b, blowing device 11d for supplying cooling air toward this heat sink 11c, and guide member 11e are disposed in mechanical room S3. In the present embodiment, dew condensation member 11a, Peltier element 11b, heat sink 11c, and blowing device 11d are disposed on the left side of sensor box 13. The cooling air that is blown from blowing device 11d and heated after cooling Peltier element 11b via heat sink 11c is guided by guide member 11e to opening 13c positioned in the left side surface of sensor box 13.

[2. Effects]

(1) As described above, in the conventional culture apparatus, the $CO_2$ sensor is disposed in the sensor box, and the air in the culture space is supplied into the sensor box through the pipe. On the other hand, in culture apparatus 1 illustrated in FIGS. 1 and 2, leading end 8a of $CO_2$ sensor 8 is exposed to culture space 20 (specifically, in duct 5). Thus, in this culture apparatus 1, the pipe for supplying air in the culture space into the sensor box is not necessary. Therefore, according to culture apparatus 1 of one embodiment of the present invention, it is possible to achieve a simpler configuration and a greater cost reduction than the conventional culture apparatus because of the unnecessity of the pipe, and it is also possible to reduce the size by omitting the space occupied by the pipe.

(2) Although space S1 (air layer 2d) in which $CO_2$ sensor 8 is inserted is sealed by packing P2, leakage flow L may occur as indicated by the arrows of dashed dotted lines in FIG. 1. That is, air in culture space 20 may flow into air layer 2d. When the air in culture space 20 flows into air layer 2d and the air stays between the light-emitting element and the light-receiving element in $CO_2$ sensor 8, this staying air becomes a factor of error for sequential measurement of $CO_2$ concentration in the air in culture space 20. Consequently, the $CO_2$ concentration in culture space 20 cannot be accurately controlled based on the detection result of $CO_2$ sensor 8. However, leakage flow L toward $CO_2$ sensor 8 is regulated by disposing sealing material 9 in space S1, and it is thus possible to reduce the measurement error in $CO_2$ concentration caused by leakage flow L, and consequently, it is possible to control the $CO_2$ concentration in culture space 20 with high accuracy.

(3) In space S1, sealed space S2 is provided around $CO_2$ sensor 8 by surrounding $CO_2$ sensor 8 with sealing material 9 (from above, below, left, and right). The presence of sealed space S2 makes it possible to effectively reduce leakage flow L reaching $CO_2$ sensor 8 to reduce the measurement error in $CO_2$ concentration more effectively.

(4) Passage 2e that communicates from sealed space S2 to the outside of outer box 2b (in this case, mechanical room S3) is formed in heat insulation material 2c of outer box 2b. It is thus possible to discharge leakage flow L from sealed space S2 even if leakage flow L passes sealing material 9 to flow into sealed space S2, so as to reduce measurement error in $CO_2$ concentration more effectively.

In particular, in the present embodiment, passage 2e is formed on the lower side in sealed space S2, and further, bottom surface 2f of passage 2e is inclined downward from sealed space S2 toward mechanical room S3 outside sealed space S2, and it is thus possible to reduce the measurement error in $CO_2$ concentration more effectively for the following reason: $CO_2$ has a greater specific gravity among the components contained in the air, and thus tends to accumulate in sealed space S2 when leakage flow L flows into sealed space S2; however, the $CO_2$ gas sequentially accumulated in sealed space S2 can be smoothly discharged to mechanical room S3 as a result of formation of passage 2e on the lower side in sealed space S2 and bottom surface 2f of passage 2e inclined downward to mechanical room S3.

(5) The effects of culture apparatus 1 will further be described with reference to FIG. 2. The arrows of thick solid lines indicate the flow of air (cooling air) sent under pressure by blowing device 11d. The arrows of thick dashed lines indicate the flow of gases (hereinafter referred to as "$CO_2$ gas") mainly containing $CO_2$ discharged into mechanical room S3 and sensor box 13 from sealed space S2.

Air (cooling air) sent under pressure by blowing device 11d cools the heating surface of Peltier element 11b cooling dew condensation member 11a, is heated, and then flows into sensor box 13 through opening 13c on the left side by the guide of guide member 11e. A part of this inflow air flows out of sensor box 13 through opening 13b formed in the bottom surface of sensor box 13. At that time, the part of the inflow air expels the $CO_2$ gas in sensor box 13 through opening 13b and flows out through opening 13b while entraining the $CO_2$ gas in sensor box 13. Another part of the air flowed into sensor box 13 expels the $CO_2$ gas in sensor box 13 through opening 13c on the right side and flows out through opening 13c while entraining the $CO_2$ gas in sensor box 13. Therefore, since the $CO_2$ gas in sealed space S2 and/or sensor box 13 is sequentially discharged, the $CO_2$ gas does not stay in sealed space S2, and it is possible to reduce the influence on measurement of $CO_2$ concentration by $CO_2$ sensor 8.

Further, the temperature of $CO_2$ sensor 8 can be maintained at an appropriate temperature by the temperature in sensor box 13 raised by the air (cooling air) having cooled the heating surface of Peltier element 11b and thus heated.

[3. Others]

Although $CO_2$ sensor 8 is surrounded from above, below, left, and right by sealing material 9, which is the regulation member, in space S1 (air layer 2d) in the above embodiment, one, two, or three regulation members may be disposed on one, two, or three of the upper, lower, left, and right sides of $CO_2$ sensor 8. Alternatively, another frame-shaped sealing material may also be disposed on the outer peripheral side of sealing material 9. That is, a plurality of sealing materials 9 surrounding $CO_2$ sensor 8 in a multilayered manner may be disposed. In short, the shape, arrangement, and number of the regulation members are not limited as long as the regulation member(s) regulate the airflow toward $CO_2$ sensor 8.

The disclosure of Japanese Patent Application No. 2018-166645, filed on Sep. 6, 2018, including the specification, claims, drawings and abstract is incorporated herein by reference in its entirety.

INDUSTRIAL APPLICABILITY

The present invention can provide a culture apparatus achieving cost reduction and size reduction. Therefore, the industrial applicability of the present invention is enormous.

REFERENCE SIGNS LIST

1 Culture apparatus
2 Heat insulation box
2a Inner box
2b Outer box
2c Heat insulation material
2d Air layer
2e Passage
2f Bottom surface
3a Outer door
3b Inner door
4 Shelf
5 Duct
5a Suction port
5b Blow-out port
5c Circulation blower
6 Humidification tray
7 Ultraviolet lamp
8 $Co_2$ sensor
8a Leading end (first end)
8b Rear end (second end)
9 sealing material (regulation member)
10 Cover
11a Dew condensation member
11b Peltier element 11c Heat sink
11d Blowing device
11e Guide member
12 Gas supply device
13 Sensor box
13a Inner space
13b Opening
13c Opening
20 Culture space
21 Opening
100 Operation device
K Gas passage
L Leakage flow
P1, P2 Packing
S1 Space (first space)
S2 Sealed space (second space)
S3 Mechanical room
W Water

The invention claimed is:

1. A culture apparatus, comprising:
a front door;
an inner box having a culture space formed inside;
an outer box covering an outside of the inner box with a first space therebetween;
a $CO_2$ sensor disposed in the first space such that a first end of the $CO_2$ sensor is exposed to the culture space; and
a sealing material that regulates a flow of a fluid toward the $CO_2$ sensor in the first space and is in direct contact with the inner box and the outer box to form a second space surrounding the $CO_2$ sensor in the first space, wherein:
the $CO_2$ sensor disposed at a rear wall of the inner box facing the front door and at a rear wall of the outer box facing the rear wall of the inner box, and
the sealing material has a frame shape surrounding the $CO_2$ sensor within the first space and is not in contact with the $CO_2$ sensor.

2. The culture apparatus according to claim 1, wherein the sealing material is in direct contact with a first face of the inner box and a second face of the outer box which faces the first face of the inner box.

3. The culture apparatus according to claim 1, further comprising:
a passage configured to discharge a gas from the second space to an outside of the outer box,
wherein the passage is disposed at the rear wall of the outer box below the $CO_2$ sensor in a vertical direction.

4. The culture apparatus according to claim 3, further comprising:
a sensor box disposed to cover a second end of the $CO_2$ sensor, the second end being an end opposite to the first end, the sensor box having an opening;
a dew condensation member inserted into the culture space; and
a Peltier element that cools the dew condensation member, wherein:
the sensor box is disposed at an outer surface of the outer box,
the second end is exposed outside the outer box,
a heating surface of the Peltier element is configured to be cooled by a cooling gas supplied through the opening, and
the passage communicates with an inner space of the sensor box.

5. A culture apparatus, comprising:
a front door;
an inner box having a culture space formed inside;
an outer box covering an outside of the inner box with a first space therebetween;
a $CO_2$ sensor disposed in the first space such that a first end of the $CO_2$ sensor is exposed to the culture space;
a sealing material that regulates a flow of a fluid toward the $CO_2$ sensor in the first space and is in direct contact with the inner box and the outer box to form a second space surrounding the $CO_2$ sensor in the first space; and
a passage configured to discharge a gas from the second space to an outside of the outer box, wherein:
the $CO_2$ sensor disposed at a rear wall of the inner box facing the front door and at a rear wall of the outer box facing the rear wall of the inner box, and
the passage is disposed at the rear wall of the outer box and located below the $CO_2$ sensor in a vertical direction.

6. The culture apparatus according to claim 5, further comprising:
a sensor box disposed to cover a second end of the $CO_2$ sensor, the second end being an end opposite to the first end, the sensor box having an opening;
a dew condensation member inserted into the culture space; and
a Peltier element that cools the dew condensation member, wherein:
a heating surface of the Peltier element is configured to be cooled by a cooling gas supplied through the opening, and
the passage further communicates with an inner space of the sensor box.

7. The culture apparatus according to claim 5, wherein the passage comprises a through hole formed in the outer box.

8. The culture apparatus according to claim 5, wherein a bottom surface of the passage comprises an inclined surface inclined downward from the second space toward the outside of the outer box.

9. The culture apparatus according to claim 5, wherein the sealing material has a frame shape surrounding the $CO_2$ sensor within the first space.

10. The culture apparatus according to claim 5, wherein a second end of the $CO_2$ sensor, which is an end opposite to the first end, is exposed outside the outer box.

* * * * *